(12) United States Patent
Swanson et al.

(10) Patent No.: US 6,357,447 B1
(45) Date of Patent: Mar. 19, 2002

(54) SURFACE COATINGS FOR CATHETERS, DIRECT CONTACTING DIAGNOSTIC AND THERAPEUTIC DEVICES

(75) Inventors: David K. Swanson, Cupertino; Yi Yang, San Francisco; James G. Whayne, Saratoga; Josef V. Koblish, Sunnyvale, all of CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

(21) Appl. No.: 09/428,237

(22) Filed: Oct. 26, 1999

Related U.S. Application Data

(63) Continuation of application No. 08/879,343, filed on Jun. 20, 1997, now Pat. No. 5,991,650, which is a continuation of application No. 08/545,105, filed on Oct. 19, 1995, now Pat. No. 6,001,093, which is a continuation of application No. 08/138,142, filed on Oct. 15, 1993, now abandoned, and application No. 08/763,169, filed on Dec. 10, 1996, now Pat. No. 6,106,822, which is a continuation of application No. 08/287,192, filed on Aug. 8, 1994, now abandoned, and application No. 08/803,431, filed on Feb. 20, 1997, now Pat. No. 6,032,061, and application No. 08/747,811, filed on Nov. 14, 1996, now Pat. No. 5,871,443, which is a continuation of application No. 08/836,174, filed on Apr. 22, 1996, now abandoned, which is a division of application No. 08/168,476, filed on Dec. 16, 1993, now Pat. No. 5,509,419, and a continuation of application No. 08/631,356, filed on Apr. 12, 1996, now Pat. No. 5,840,076, and application No. 08/631,252, filed on Apr. 12, 1996, now Pat. No. 5,797,903, and application No. 08/630,719, filed on Apr. 8, 1996, now abandoned.

(60) Provisional application No. 60/010,356, filed on Jan. 19, 1996, and provisional application No. 60/010,225, filed on Jan. 19, 1996.

(51) Int. Cl.⁷ .............................................. A61B 19/00
(52) U.S. Cl. .......................... 128/898; 600/374; 606/41
(58) Field of Search .............................. 606/41, 42, 49, 606/52; 600/372, 374; 128/898; 604/264, 265

(56) References Cited

U.S. PATENT DOCUMENTS

| | | | |
|---|---|---|---|
| 3,635,212 A | * | 1/1972 | Watanabe et al. |
| 5,016,808 A | | 5/1991 | Heil, Jr. et al. |
| 5,304,120 A | | 4/1994 | Crandall et al. |
| 5,364,404 A | | 11/1994 | Jaffe et al. |
| 5,403,295 A | | 4/1995 | Byrne |
| 5,403,311 A | | 4/1995 | Abele et al. |
| 5,411,544 A | | 5/1995 | Mar et al. |
| 5,462,545 A | | 10/1995 | Wang et al. |
| 5,471,982 A | | 12/1995 | Edwards et al. |
| 5,545,161 A | | 8/1996 | Imrán |
| 5,607,422 A | | 3/1997 | Smeets et al. |
| 5,797,903 A | * | 8/1998 | Swanson et al. ............ 606/34 |
| 6,106,889 A | * | 8/2000 | Beavers et al. ............ 427/2.1 |
| 6,212,426 B1 | * | 4/2001 | Swanson .................... 600/510 |
| 6,221,061 B1 | * | 4/2001 | Engelson et al. ........... 604/265 |

FOREIGN PATENT DOCUMENTS

| | | | |
|---|---|---|---|
| CA | 1173116 | 8/1984 | |
| EP | 0 346 058 A1 | 6/1989 | ............ A61N/1/20 |
| WO | WO 92/20396 | 11/1992 | |
| WO | WO 94/15581 A | 7/1994 | |
| WO | WO 98/09667 | 3/1998 | |

* cited by examiner

Primary Examiner—Michael Peffley
(74) Attorney, Agent, or Firm—Lyon & Lyon LLP

(57) ABSTRACT

A method for manufacturing a catheter assembly including a handle, a guide tube having a proximal end engaged with the handle, and a distal end assembly engaged with a distal end of the guide tube. The method includes applying an active electrode element on the distal end assembly by a process selected from the group consisting of electroplating, vapor deposition, IBAD and pad printing, and applying a regenerated cellulose coating over the distal end assembly. The regenerated cellulose coating is applied by applying a viscous liquid coating to the catheter distal end assembly, regenerating the viscous coating, and then curing the regenerated coating. The cured coating is preferably hydrated.

5 Claims, 6 Drawing Sheets

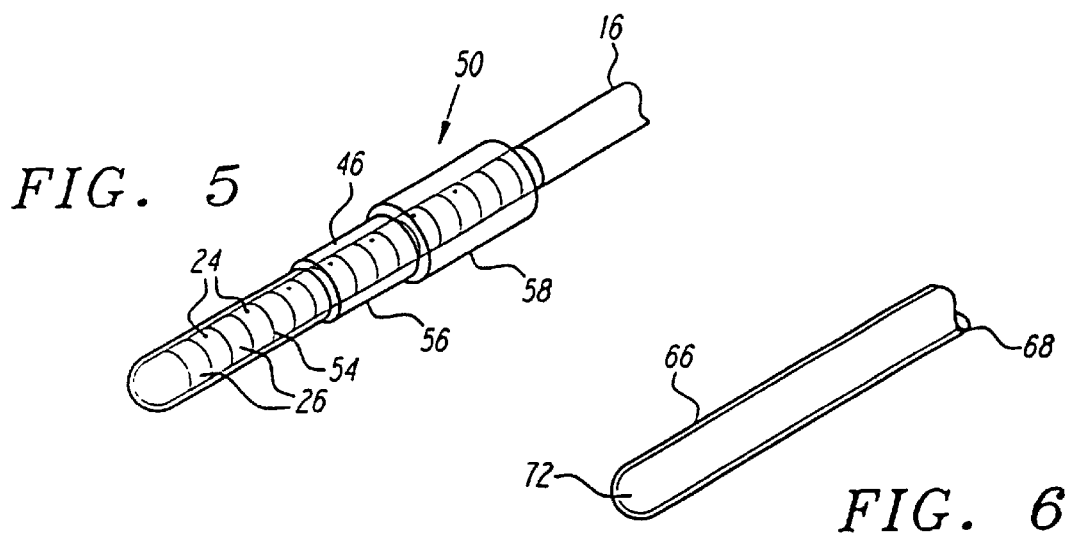
FIG. 5
FIG. 6
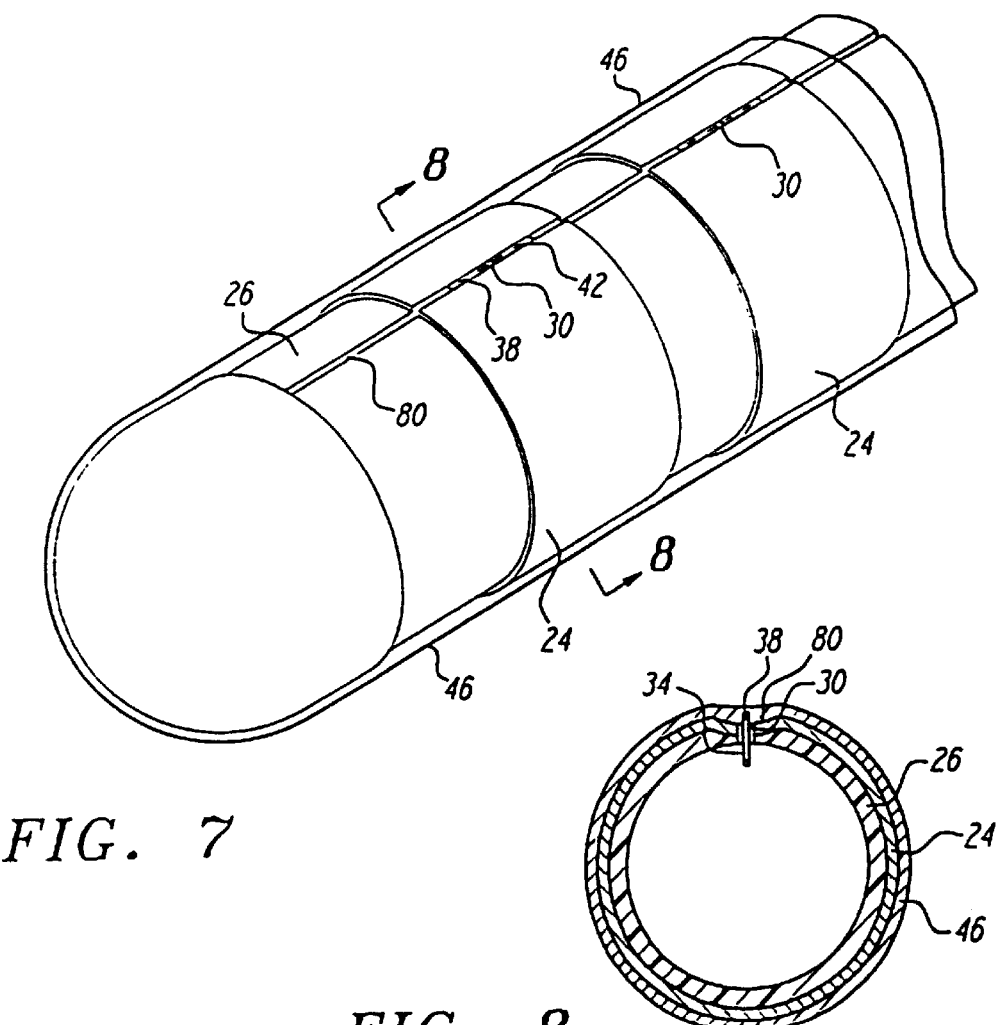
FIG. 7
FIG. 8

SURFACE COATINGS FOR CATHETERS, DIRECT CONTACTING DIAGNOSTIC AND THERAPEUTIC DEVICES

CROSS REFERENCE TO RELATED APPLICATIONS

This application is a continuation of application Ser. No. 08/879,343, filed Jun. 20, 1997, now U.S. Pat. No. 5,991,650 of U.S. patent applications Ser. Nos. 08/545,105 filed Oct. 19, 1995, now U.S. Pat. No. 6,001,093 which is a continuation of Ser. No. 08/138,142, filed Oct. 15, 1993, now abandoned, entitled "Systems and Methods for Creating Long, Thin Lesions in Body Tissue; U.S. patent application Ser. No. 08/763,169, filed Dec. 10, 1996 now U. S. Pat. No. 6,106,822 which is a continuation of Ser. No. 08/287,192, filed Aug. 8, 1994, now abandoned, entitled "Systems and Methods for Forming Elongated Lesion Patters in Body Tissue using Straight or Curvilinear Electrode Elements; U.S. patent application Ser. No. 08/803,431, filed Feb. 20, 1997, now U.S. Pat. No. 6,032,061, entitled "Catheter Carrying and Electrode and Methods of Assemblies"; U.S. patent application Ser. No. 08/747,811, filed Nov. 14, 1996 now U.S. Pat. No. 5,871,443 which is a continuation of Ser. No. 08/636,174, filed Apr. 22, 1996 abandoned, which is a divisional of U.S. patent application Ser. No. 08/168,476, filed Dec. 16, 1993 now U.S. Pat. No. 5,509,419, issued Apr. 23, 1996, filed Dec. 16, 1993 entitled "Cardiac Mapping and Ablation Systems"; U.S. patent application Ser. No. 08/630,719 filed Apr. 8, 1996, claiming priority of U.S. provisional application Ser. No. 60/010,354, filed Jan. 19, 1996, entitled "Expandable-Collapsible Electrode Structures with Electrically Conductive Walls"; U.S. patent application Ser. No. 08/631,356, filed Apr. 12, 1996, now U.S. Pat. No. 5,840,076, claiming priority of U.S. Provisional Patent Application Ser. No. 60/010,225, filed Jan. 19, 1996, entitled "Tissue Heating and Ablation Systems and Methods Using Electrode Structures with Distally Oriented Porous Lesions"; and U.S. patent application Ser. No. 08/631,252, filed Apr. 12, 1996, now U.S. Pat. No. 5,797,903 which claims priority of U.S. Provisional Application Ser. No. 60/010,225, filed Jan. 19, 1996, entitled "Tissue Heating and Ablation Systems and Methods Using Porous Electrode Structures with Electrically Conductive Surfaces".

BACKGROUND OF THE INVENTION

1. Field of the Invention

The present invention relates generally to catheter distal end assemblies, and more particularly to surface coatings for such assemblies.

2. Description of the Prior Art

Conventionally, catheter components such as electrodes and thermocouples are placed onto electrophysiology catheters manually. The electrodes are then held in position and masked with adhesive. This process is very time consuming and thus quite expensive. An undesirable feature of such a catheter-electrode construction for ablation is that it has high electrode edge effects that are attributed to delivering RF energy to an electrode having a sharp transition between the conductive electrode and the insulating catheter body. A further limitation in the prior art is that toxic materials such as those composed of silver and lead, cannot be used where direct contact with the patient's tissues and bodily fluids occur. Additionally, many prior art catheter devices are formed with small openings and crevices which permit the ingress and retention of bodily fluids and tissue. There is therefore a need for a surface coating for catheter distal end assemblies that solves these problems.

SUMMARY OF THE INVENTION

A catheter of the present invention includes a distal end assembly having an external surface coating. Where the distal end assembly includes electrodes or other electrical components, the coating is preferably electrically conductive. In the preferred embodiment, such an electrically conductive coating is formed from a material comprising regenerated cellulose, although other materials such as a hydrogel or a plastic having an electrically conductive component are utilizable. Where the distal end assembly includes optical or ultrasonic components, the preferred surface coating is substantially transparent to optical and ultrasonic transmissions therefrom. A regenerated cellulose coating is suitable for both optical and ultrasonic distal end assemblies.

The robustness of the surface coating permits the manufacture and utilization of electrode configurations that are formed on a non-conductive base member by processes such as pad printing, vapor deposition, ion beam assisted deposition, electroplating and other printed circuit manufacturing processes. Additionally, because the surface coating produces a smooth outer surface to the distal end assembly, lead wires and temperature sensing devices can be bonded to the exterior surface of electrodes and then coated to produce a smooth outer surface; thus providing a simple, inexpensive manufacturing method for the attachment of such components to the electrodes.

It is an advantage of the present invention that catheter distal end assemblies can be more efficiently manufactured.

It is another advantage of the present invention that catheter distal end assemblies can be more inexpensively manufactured.

It is a further advantage of the present invention that electrode configurations can be printed or deposited upon the surface of a catheter end assembly and withstand the mechanical and chemical stresses of usage without degradation.

It is yet another advantage of the present invention that catheter distal end assemblies having a surface coating are sealed against ingress of contaminating bodily fluids.

These and other features and advantages of the present invention will become obvious to those of ordinary skill in the art upon reading the following detailed description.

IN THE DRAWINGS

FIG. 5 is a perspective view of a catheter distal end assembly having a surface coating having a variable thickness;

FIG. 6 is a perspective view of a regenerated cellulose casing for use as a surface coating for a catheter distal end assembly;

FIG. 7 is a perspective view of a catheter distal end assembly formed with a skive for the disposition of electrical interconnections, and having a surface coating;

FIG. 8 is a cross-sectional view taken along lines 8—8 of FIG. 7;

DETAILED DESCRIPTION OF THE PREFERRED EMBODIMENTS

Figure 1:
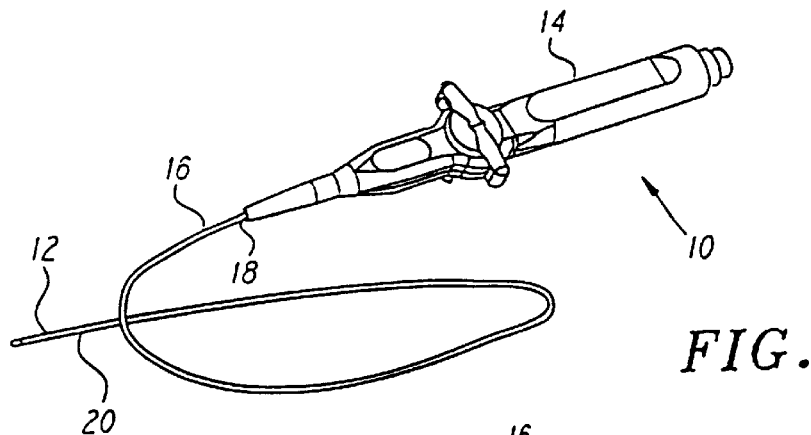
FIG. 1 is a perspective view of a catheter device having a distal end assembly having a surface coating thereon.

The present invention includes the use of a coating forming an external surface for catheters, direct contacting medical devices, and similar instruments, as well as a surface coating over components of such catheters and similar instruments. A particular application of the present invention involves using regenerated cellulose as a coating material for forming an external surface for catheter devices used for pacing, recording, and delivering RF energy. These catheter devices include devices that are capable of creating long, thin lesions of different curvilinear shapes, and devices that are capable of creating large, deep lesion patterns in heart tissue. Such devices are described in U.S. Pat. No. 5,582,609, issued Dec. 12, 1996, entitled: "Systems and Methods for Forming Large Lesions in Body Tissue Using Curvilinear Electrode Elements", U.S. patent application Ser. No. 08/763,169, entitled: "Systems and Methods for Forming Elongated Lesion Patterns in Body Tissue Using Straight or Curvilinear Electrode Elements"; U.S. patent application Ser. No. 08/545,105, entitled: "Systems and Methods for Creating Long, Thin Lesions in Body Tissue", the disclosures of each of these references being incorporated herein by reference as thought set forth in full. It is also to be appreciated that the invention is applicable for use in other tissue ablation applications. For example, various aspects of the invention have application in procedures for ablating tissue in the prostate, brain, gall bladder, uterus, and other regions of the body, using systems that are not necessarily catheter-based.

The regenerated cellulose coating acts as a mechanical barrier between the catheter components, such as electrodes, preventing ingress of blood cells, infectious agents, such as viruses and bacteria, and large biological molecules such as proteins, while providing electrical contact to the human body: As a result the electrodes can now be made using more efficient processes (such as pad printing) that have been previously rejected due to lack of robustness when directly exposed to bodily tissues on a catheter surface. The regenerated cellulose coating also acts as a biocompatible barrier between the catheter components and the human body, whereby the components can now be made from materials that are somewhat toxic (such as silver or copper), because the diffusional distance to tissues is increased substantially, and because a lower percentage of the metallic surface is exposed (both directly and indirectly) to the tissue. In addition, coating electrodes with regenerated cellulose decreases the effect of convective cooling on the electrode. That is, since regenerated cellulose is a poor thermal conductor when compared to metal, the effect of convective cooling by blood flowing past the regenerated cellulose coated electrodes is diminished. This provides better control for the lesion-generating process because the hottest tissue temperature is closer to the ablation electrode. Furthermore, the regenerated cellulose coating decreases the edge effects attributed to delivering RF energy to an electrode having a sharp transition between the conductive electrode and insulating catheter tubing. The current density along the electrode and power density within tissue are more uniform, which reduces the incidence and severity of char and/or coagulum formation. The more uniform current density along the axis of the catheter also results in a more uniform temperature distribution at the electrode, which decreases the requirement for precise placements of the temperature sensors at the ablation electrodes. Furthermore, by coating a catheter with regenerated cellulose to create the outer catheter surface, less labor-intensive methods to form electrodes and for bonding wires to electrode surfaces can be used.

In the coating process of the present invention a device, such as a catheter distal assembly with components such as electrodes and wire conductors fixed in place, is coated with a viscose solution. In the preferred embodiment the viscose solution is cellulose xanthate, which is a form of solubilized cellulose derivative that is dissolved in a sodium hydroxide solution. The viscose solution is dip-coated onto the distal end assembly, which includes the electrodes, signal wires, temperature sensors and distal tubing. The catheter coated with the cellulose xanthate derivative is then regenerated by contacting it with an acid, such as sulfuric acid, which converts the xanthate back into the cellulose structure. The term regenerated cellulose refers to cellulose which has been converted from a solubilized cellulose derivative back into a pure cellulose structure. This regeneration process creates large enough micro size pores in the coating allowing ionic transport yet small enough to prevent ingress of blood cells, infectious agents, such as viruses and bacteria, and large biological molecules such as proteins.

Once the cellulose is regenerated, it is rinsed with water to remove acid residuals and sulfur compounds. An oxidizing agent (bleach, etc.) may be added to the rinse water to accelerate the removal of sulfur compounds. After the cellulose is regenerated, it is fully cured in an environmental chamber at a low humidity. Thereafter, it is preferable to make the regenerated cellulose flexible when dry, and to do so moisture is reintroduced into the cellulose coating material by setting the environmental chamber to a higher humidity. Alternatively, a small quantity of a material such as glycerol may be applied to the coating, and the hydroscopic nature of the glycerol will hydrate the cellulose coating to create sufficient flexibility. An overall thickness range for operable regenerated cellulose coatings is from 0.001 inches to 0.015 inches, with a preferable thickness range being from 0.001 inches to 0.003 inches; a preferred thickness being approximately 0.002 inches.

Materials other than regenerated cellulose that are mechanically robust and that have suitable characteristics could be used for the coating material. Hydrophilic materials that have effective pore sizes from 500 to 500,000 Daltons with a porosity of 1–10% and which are biocompatible could be effective. Some types of hydrogels, such as those used for disposable contact lenses are good candidate materials. Plastic materials that have additives to make them semiconductive could also be used. The loaded plastic would need to have a resistivity in the range of about 200–2,000 ohm-cm, and would need to be appliable in very thin films to the catheter body.

FIG. 1 depicts a catheter device 10 of the present invention that includes a catheter distal section 12 of the present invention. As shown therein, the catheter 10 generally includes a handle 14, a guide tube 16 having a proximal end 18 engaged to the handle 14, and having a distal end 20 to which the distal section 12 is engaged. As is described hereinbelow in detail, the distal end section 12 is formed with a regenerated cellulose coating.

Figure 2:
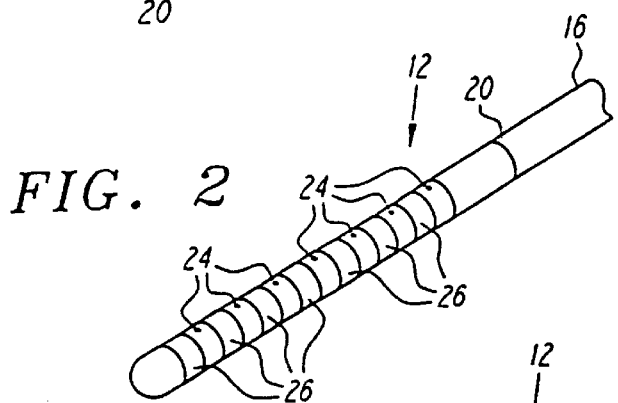
FIG. 2 is an enlarged perspective view the distal end assembly of FIG. 1.
Figure 3:
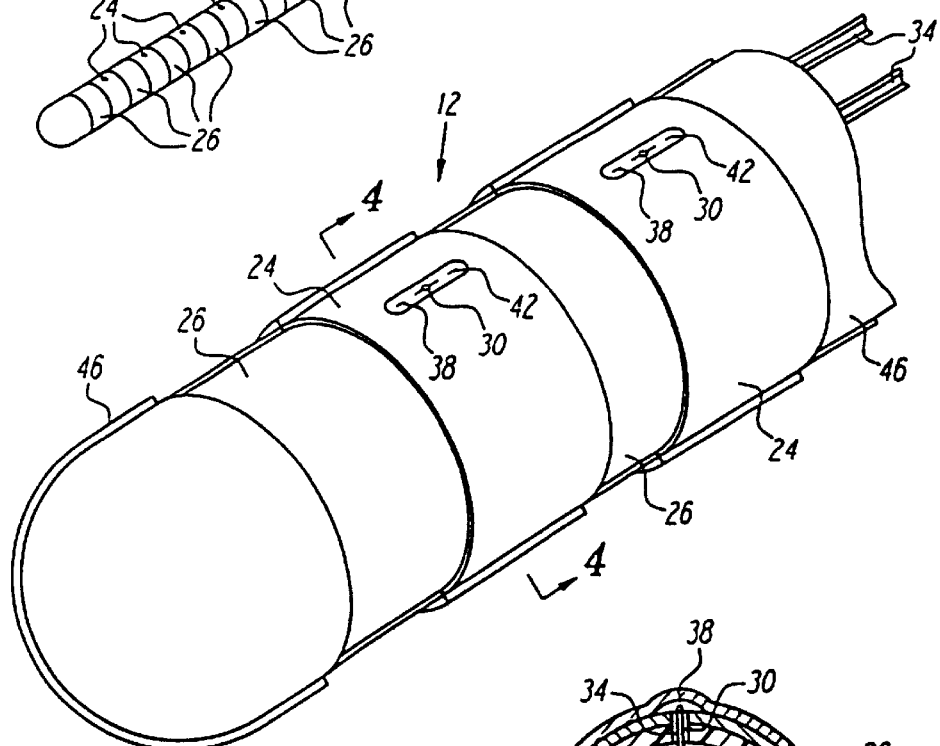
FIG. 3 is a further enlarged view of the distal end assembly depicted in FIG. 2.
Figure 4:
FIG. 4 is a cross-sectional view taken along lines 4—4 of FIG. 3.

A catheter distal end 12 comprising a preferred embodiment is depicted in FIGS. 2, 3 and 4, wherein FIG. 2 is a perspective view, FIG. 3 is an enlarged view of the distal end section, and FIG. 4 is a cross-sectional view taken along lines 4—4 of FIG. 3. The catheter distal end 12 includes a plurality of electrodes 24 which in this embodiment 12 are formed with a conductive ink compound that is pad printed onto a non-conductive tubular body portion 26. A preferred conductive ink compound is a silver-based conductive ink epoxy, however other metal based conductive ink epoxies such as platinum-based, copper-based, etc., may also be used to form electrodes. A platinum-based conductive ink epoxy may also be used to increase the radiopacity of the electrodes, and electrodes may also be formed by pad printing multiple layers of different metal based conductive ink epoxies.

As is best seen in FIG. 4, hole 30 is created through a single wall of the body tubing 26 in each of the conductive ink band electrodes 24, and a lead wire/thermocouple wire ribbon 34 is pulled through the hole 30. The insulation at the ends of the lead wire 38 and thermocouple 42 is stripped, and the stripped lead wire 38 and thermocouple assembly 42 are separated and placed over the conductive ink band electrode 24 and glued at the hole 30 for fixation. The thermocouple 42 is electrically insulated from the electrode 24, whereas the lead wire 38 is electrically connected to the electrode 24, such as by using a conductive adhesive. Also a small amount of the conductive ink may be placed over the lead wire 38, electrically bridging it to the ink band electrode 24. The finished sub-assembly is then coated with regenerated cellulose 46 in the manner described above to establish its external surface. The devices and methods disclosed in U.S. patent application Ser. No. 08/803,431 may also be advantageously covered with the coating of the present invention and the disclosure of said application is incorporated herein by reference as though set forth in full.

The thickness of the cellulose coating 46 is controlled by the viscosity of the coating solution and the dipping rate, and a different viscosity of the coating solution can be achieved by diluting it with the sodium hydroxide solution. A variable wall thickness can be achieved by varying the extraction rate during the dipping process. The slower the extraction rate, the thinner the wall thickness, and the faster the extraction rate, the thicker the wall thickness. FIG. 5 depicts a catheter distal end section 50 having such a variable wall thickness. Specifically, the distal end section 50 includes electrodes 24 formed upon a tubular distal body portion 26. The regenerated cellulose coating 46 includes a thin distal section 54, a thicker middle section 56 and a thickest proximal section 58.

To form this variable wall thickness, the distal end assembly is dipped tip first into the coating solution, and it is removed most rapidly at first to form the thick section 58, more slowly to form the thinner middle section 56, and slowest to form the thin distal section 54.

An increased coating wall thickness can also be obtained by multiple layers of coating. To ensure proper lamination between such layers, each layer is coagulated with a salt solution (sodium sulfate, etc.) before applying another layer. The regeneration process described above is only conducted when the desired wall thickness is achieved. A catheter distal end section having a multiple layer coating is visually identical to the distal end section 50, wherein the thin coating section 54 comprises a single layer, the middle section 56 is formed with two layers and the thickest section 58 is formed with three layers. In addition to the dipping process, spraying and co-extruding the viscose solution over the electrodes and the distal section can also be used to achieve a variable wall thickness cellulose coating.

In another method for covering a catheter distal end assembly, a tubular casing of regenerated cellulose material is created and the regenerated cellulose casing is shrunk onto the distal end assembly. Such a regenerated cellulose casing 66 is depicted in FIG. 6. It comprises a tubular member having a thin wall 68 and a rounded end 72. This method for covering a cathode distal end assembly eliminates the need to regenerate the cellulose together with the electrodes 24 and the distal body 26. In this method, the viscose cellulose solution is initially coated onto a mandrel (not shown) of appropriate outside diameter (OD) that is slightly smaller than the OD of the electrode assembly. The distal tip of the mandrel is rounded to match the shape of the electrode assembly distal tip. Once the mandrel is coated with the viscose solution to a desired wall thickness, the coated mandrel then receives the standard regeneration process described above. After the regenerated cellulose is fully cured, the casing is removed from the mandrel. The casing is then preferably dried under internal pressure to orient its fibers radially. By radially orienting the fibers, the strength of the regenerated cellulose is increased and the coating material is given a "memory". Before putting the regenerated cellulose casing 66 onto the distal end assembly, the casing is wetted which causes it to expand radially so that it has enough clearance to slide over the assembly. The entire assembly is then put in an oven to dry the cellulose casing, whereupon its memory causes it to shrink onto the assembly. The cellulose casing may then additionally be bonded to the assembly at its proximal end with an adhesive (cyanoacrylate, etc.). Additionally, an adhesive may be applied to the distal section prior to shrinking the casing to provide attachment along the distal section. An adhesive such as cyanoacrylate, that can be reactivated with heat, may be coated onto the distal section and cured prior to shrinking the casing. Once the casing is shrink onto the distal tubing, the adhesive may then be reactivated with heat to attach the casing along the distal section.

By using regenerated cellulose coating to create the final catheter external surface, less labor-intensive methods may be used to bond lead wires and thermocouples to the electrode surface. For instance, as is depicted in FIGS. 3 and 4 a lead wire 38 may be welded or soldered to the outside surface of each catheter electrodes 24 prior to applying the regenerated cellulose coating. In yet another method, as depicted in FIGS. 7 and 8, the tubular member 26 may be extruded with a longitudinal channel or skive 80 formed in its external surface. The electrodes 24 that are formed on the distal tubing 26 conform to the skive 80, and the lead wire hole 30 is formed within the skive 80, as is best seen in FIG. 8. The stripped lead wire and thermocouple ends are then bent into the skive 80 and bonded to the electrode, as discussed hereabove and depicted in FIGS. 3 and 4. A regenerated cellulose coating is then applied to the external surface of the catheter distal section as described herein. As is best seen in FIG. 8, the regenerated cellulose layer 46 fills the skive such that the exterior surface is generally smooth; it particularly does not possess an outwardly projecting bump at the location of the lead wire and thermocouple bonding, as does the embodiment depicted in FIGS. 3 and 4.

With the protection of regenerated cellulose coating, the electrodes can be made by many different techniques. For instance, the electrodes made out of conductive ink can be printed onto the catheter tubing as was discussed above with regard to FIGS. 2–8. Additionally, metallic electrodes can be plated onto the catheter tubing by various well known deposition technologies such as electroplating, ion beam assisted deposition (IBAD), vapor deposition, etc. Various electrode configurations and manufacturing methods that can be advantageously protected utilizing a coating of the present invention include those taught in U.S. Pat. No. 5,471,982, entitled: "Cardiac Mapping and Ablation Systems", issued Dec. 5, 1995. The electrodes can also be made using printed circuit technology, especially using flex circuits. Such flex circuits can be embedded in the catheter tubing throughout the entire catheter body and selectively exposed at the distal end of the catheter as electrodes by removing the insulation layer of the flex circuits with a laser. Such processes can be highly automated for cost and efficiency. Additionally, radio opaque markers and stripes can be advantageously applied to the surface of a catheter distal end assembly and covered with a regenerated cellulose coating of the present invention to provide a protective outer coating for the device.

Figure 9:
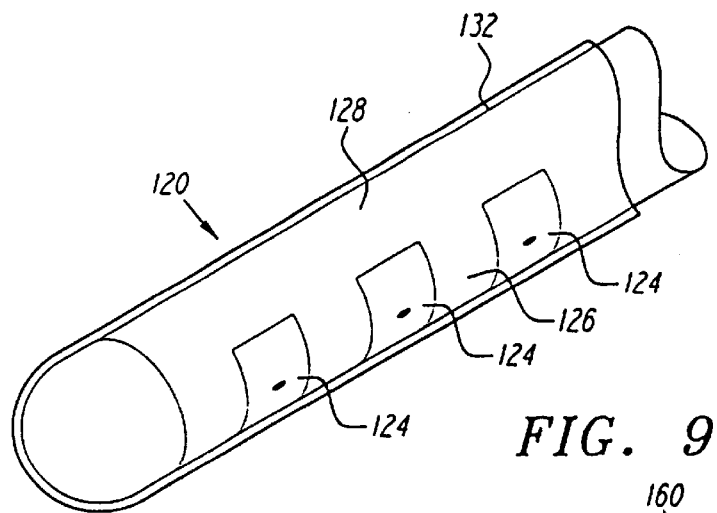
FIG. 9 is a perspective view of another catheter distal end assembly that is covered with a surface coating.

All these techniques mentioned above can make different sizes and shapes of electrodes. For example, as depicted in FIG. 9 a catheter distal end assembly 120 may be formed having the electrodes 124 only on one side 126 of the catheter body 128 to improve the efficiency of RF transmission by decreasing the surface area of the electrodes 124 and therefore decreasing the power requirements and directing the RF energy to the tissue adjacent to the exposed side 126 of the catheter 120. The regenerated cellulose coating 132 serves to protect the electrodes and facilitate the manufacturing and use of the device.

Figure 10:
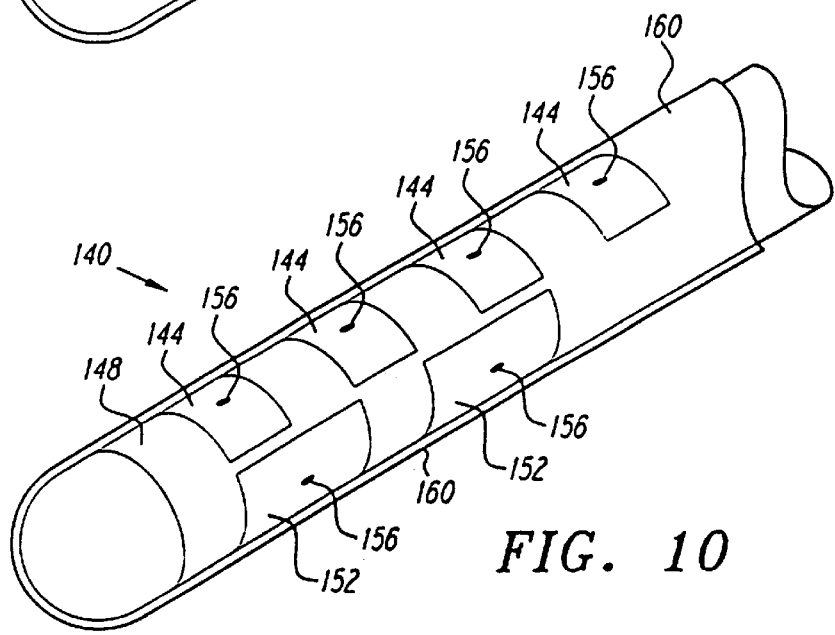
FIG. 10 is a perspective view of a further catheter distal end assembly that is covered with a surface coating.

Other electrode configurations and combinations are made possible by the utilization of the regenerated cellulose coating of the present invention. FIG. 10 depicts a catheter distal end assembly 140 having a combination of sensing electrodes 144 disposed on one side of a distal end body 148, and ablation electrodes 152 disposed on the opposite side of the body 148. Electrical connection points 156 for lead wires to the various electrodes are provided, and a regenerated cellulose coating 160 is utilized to cover the components of the distal end assembly 140.

Figure 11:
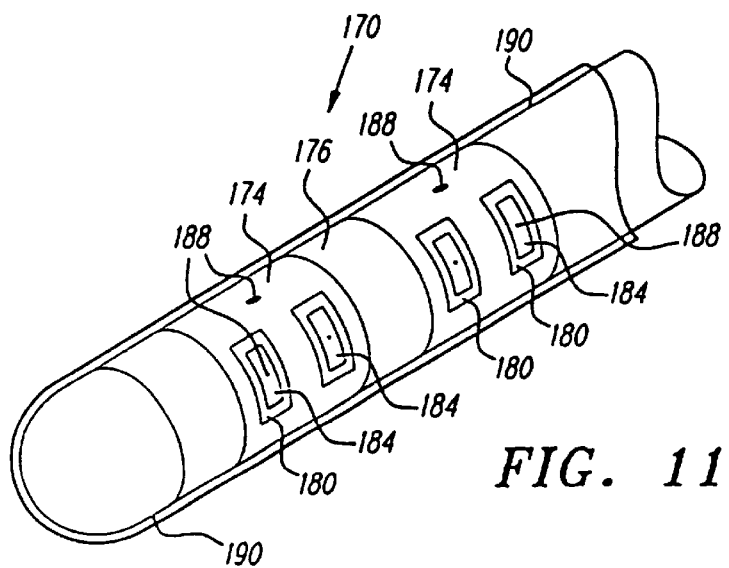
FIG. 11 is a perspective view of another catheter distal end assembly having a surface coating.

A further electrode assembly for a catheter distal end member 170 is depicted in FIG. 11, wherein ablation electrodes 174 are formed on a catheter distal end body 176. One or more windows 180 are formed in the ablation electrodes 174 and sensing electrodes 184 are disposed within the windows 180. Appropriate lead wires are connected to the various electrodes at connection points 188. The sensing electrodes 184 are insulated from the ablation electrodes 174 due to the electrically non-conductive nature of the catheter body 176. The assembly is coated with a regenerated cellulose coating 190, which facilitates the manufacturing and usage of the device 170.

Figure 12:
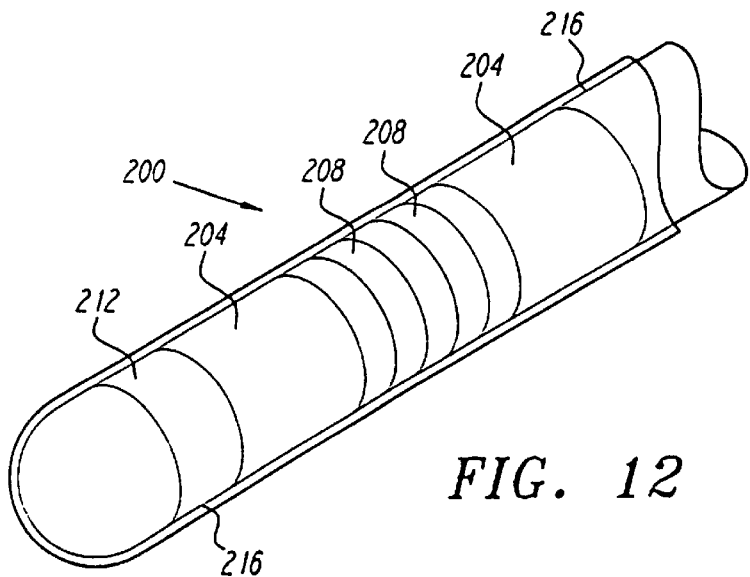
FIG. 12 is a perspective view of a further catheter distal end assembly that is covered with a surface coating.

A further electrode configuration for a catheter distal end assembly 200 is depicted in FIG. 12, wherein ablation electrodes 204 and sensing electrodes 208 are disposed in series along the tubular body 212. Again, a regenerated cellulose coating 216 over the electrodes 204 and 208 serves to facilitate the manufacturing and usage of the catheter distal end assembly 200.

Figure 13:
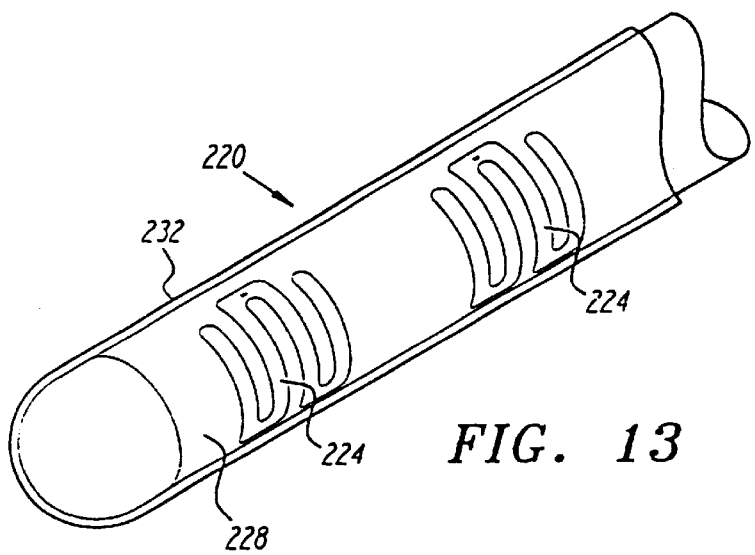
FIG. 13 is a perspective view of yet another catheter distal end assembly having serpentine shaped electrodes that are covered with a surface coating.

The utilization of the regenerated cellulose coating permits the manufacturing and usage of even more advanced electrode forms. FIG. 13 depicts a catheter distal end assembly 220 having serpentine shaped electrodes 224 formed on a tubular body member 228. A regenerated cellulose coating 232 is formed over the electrodes 224 and body portion 228.

Figure 14:
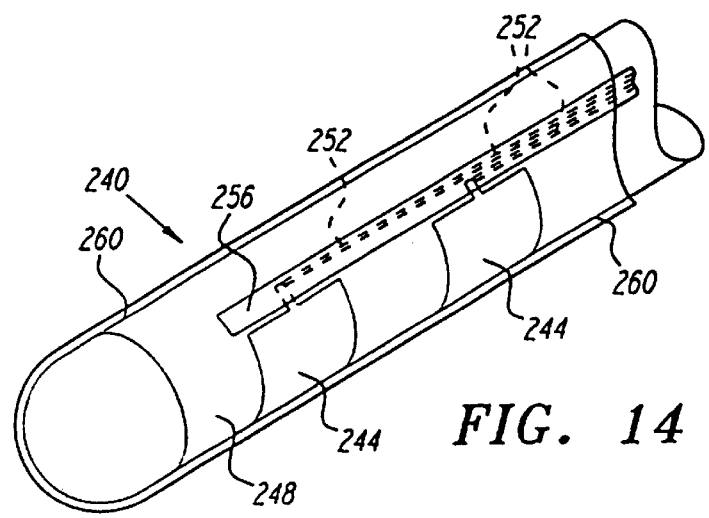
FIG. 14 is a perspective view of another catheter distal end assembly having printed circuit electrodes and lead lines that is covered with a surface coating.

Still another electrode distal end assembly 240 is depicted in FIG. 14. The assembly 240 includes a plurality of electrodes 244 that are formed on the surface of a tubular body member 248. Electrical connection members 252 for the electrodes 244 are also formed on the surface of the catheter body member 248. The electrodes 244 and their electrical connectors 252 are preferably formed in a single printing or deposition process upon the body portion 248. Thereafter, in a second printing or deposition process an insulating layer 256 is deposited on top of the electrical connectors 252 to electrically isolate the connectors 252 from electrical noise and interference. A regenerated cellulose coating 260 covers the components of the device to facilitate manufacturing and usage of the catheter end assembly 240.

Figure 15:
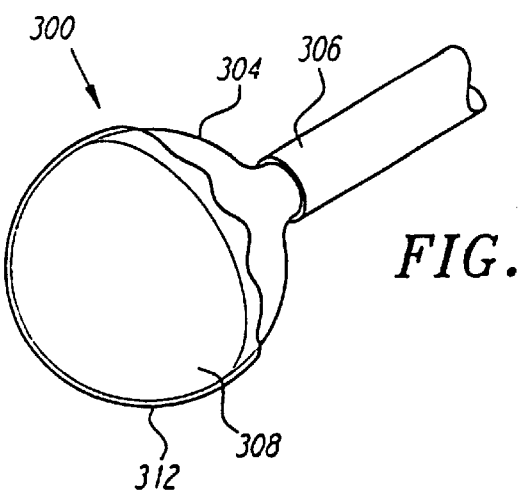
FIG. 15 is a perspective view of a balloon catheter device having a surface coating.

FIG. 15 depicts a balloon catheter end assembly 300 of the present invention. As depicted therein, an inflated balloon member 304 projects from the distal end of a catheter member 306 and has an electrode 308 formed thereon. While the electrode 308, as depicted in FIG. 15, is generally hemispherically shaped, balloon electrodes 308 having different shapes, such as rings, spirals and segments are included within this disclosure. Such devices are described in U.S. patent application Ser. No. 08/630,719, entitled "Expandable-Collapsible Electrode Structures with Electrically Conductive Walls", and U.S. patent application Ser. No. 08/631,356, entitled "Tissue Heating and Ablation Systems and Methods Using Electrode Structures with Distally Oriented Porous Regions", and U.S. patent application Ser. No. 08/631,252, entitled "Tissue Heating and Ablation Systems and Methods Using Porous Electrode Structures with Electrically Conductive Surfaces", the disclosures of which is incorporated herein by reference as though set forth in full. A regenerated cellulose coating 312 is formed over the electrode 308 to cover the entire surface of the electrode 308. The coating 312 is sufficiently strong and flexible to adhere to the balloon member 304 and the electrode surface 308 when the balloon is in its collapsed configuration as well as its expanded configuration depicted in FIG. 15, whereby the surface coating 312 serves to facilitate the manufacturing and usage of the balloon catheter embodiment 300.

Figure 16:
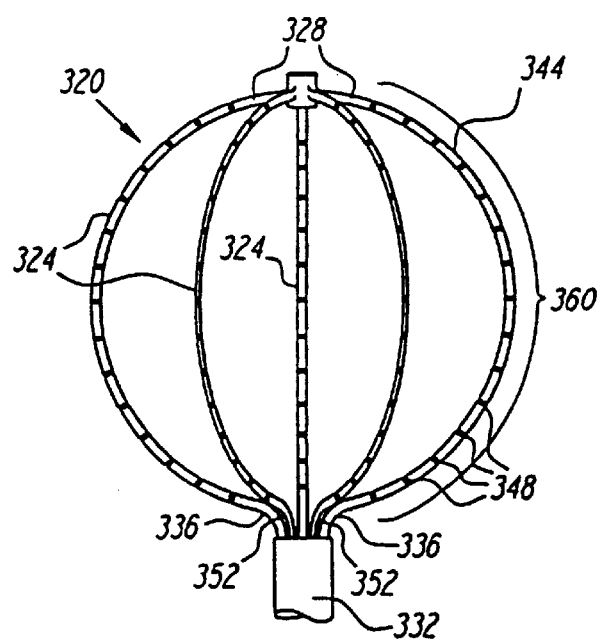
FIG. 16 is a elevational view of a catheter distal end assembly having a basket electrode array that is covered with a surface coating.
Figure 17:
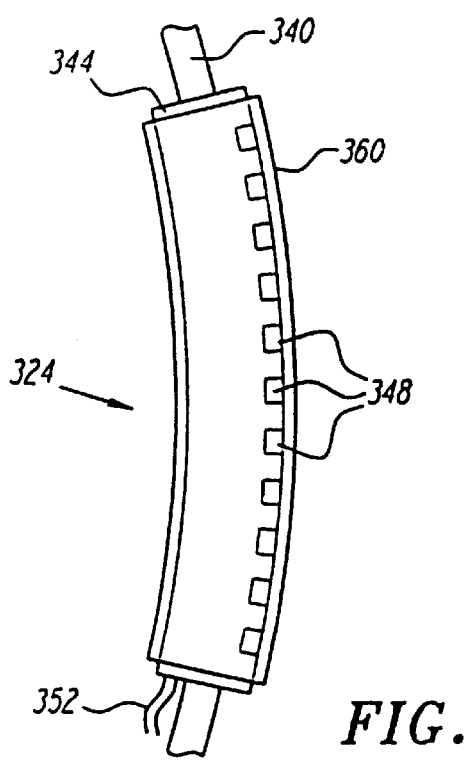
FIG. 17 is an enlarged view of one of the splines of the basket electrode array depicted in FIG. 16.

FIGS. 16 and 17 depict a catheter distal end basket assembly 320 of the present invention, wherein FIG. 16 depicts a deployed basket assembly having a plurality of spline electrode members 324, and FIG. 17 is an enlarged view of a single spline member 324. As depicted in FIGS. 16 and 17, a deployed catheter distal end basket 320 includes a plurality of spline members 324 that are pivotally joined together at their distal ends and held within a catheter basket sheath member 332 at their proximal ends 336. Each spline member 324 includes a resilient spline core body 340 that projects through a flexible tubular, non-conductive sleeve member 344 which has a plurality of electrode members 348 disposed upon the exterior, convex surface thereof. Electrode lead wires 352 are interconnected to each electrode 348. The electrode members 348 may be formed by several methods including deposition and pad printing methods. A regenerated cellulose coating 360 is formed to cover all of the electrodes 348 and sleeve 344 disposed upon each spline 324. The proximal and distal ends of each spline-core body 340 are preferably not coated with regenerated cellulose in order to better permit the mechanical pivoting and interaction of the core body end portions with other spline components.

Figure 18:
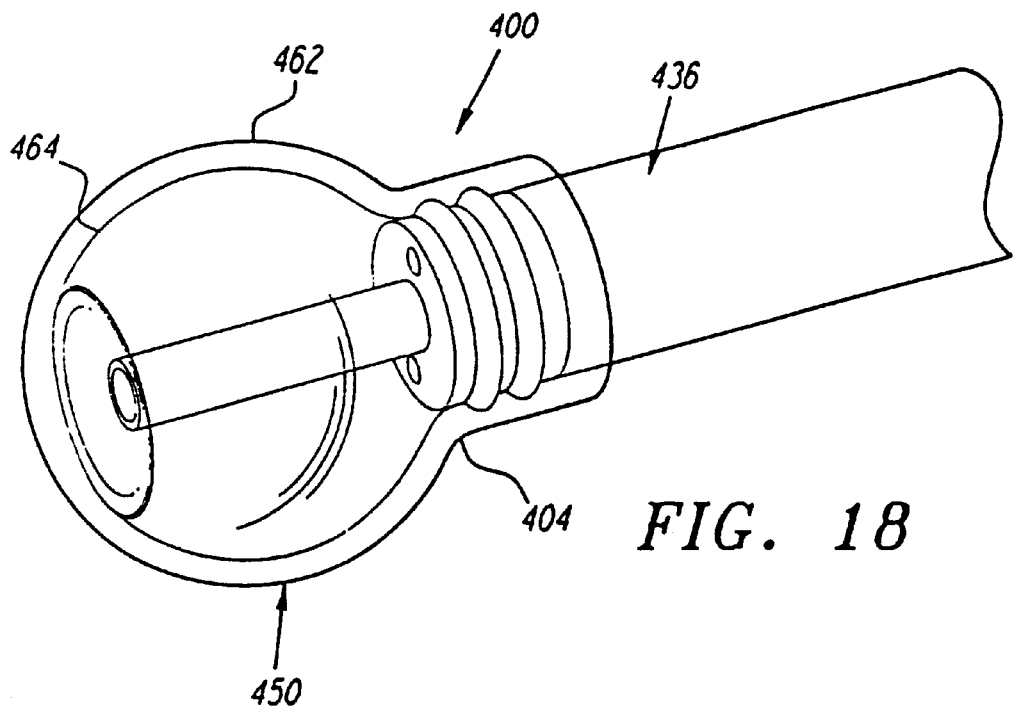
FIG. 18 depicts an optical imaging probe having a surface coating thereon.

The catheter distal end surface coating of the present invention also provides advantages for optical and ultrasonic catheter distal end components. FIG. 18 depicts an optical imaging probe assembly 400 having a surface coating 404 of the present invention formed thereon. Such an optical probe is depicted and described in copending U.S. patent application Ser. No. 08/739,039 entitled "Systems and Methods Using a Porous Electrode for Ablating and Visualizing Interior Tissue Regions", the disclosure of which is incorporated herein at this point as though set forth in full. Briefly, the imaging probe 400 includes an image acquisition element 450 includes a fiberoptic assembly 462 which permits direct visualization of tissue through a transparent balloon 464 carried at the end of a flexible body 436. The surface coating 404 is therefore preferably substantially optically transparent such that the imaging process is not affected. However, the coating 404 serves to seal the device 400 from bodily fluid ingress and provides both lubrication and robustness to the outer surface of the device 400.

Figure 19:
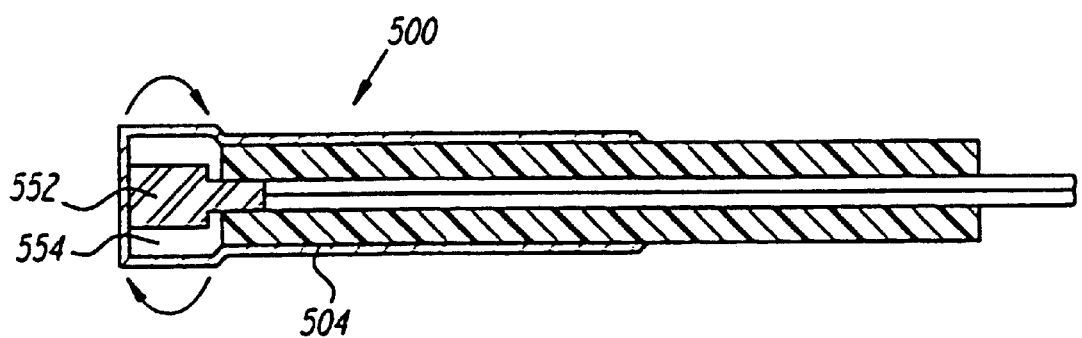
FIG. 19 depicts an ultrasonic imaging probe having a surface coating thereon.

An ultrasonic transducer embodiment 500 having a surface coating 504 is depicted in FIG. 19. The device 500 includes a catheter body portion having an ultrasonic transducer 552 disposed at its distal tip. Such an ultrasonic imaging device 500 is depicted and described in copending U.S. patent application Ser. No. 08/739,039, referenced above. Briefly, the ultrasonic transducer 552 is disposed to rotate within a chamber formed by chamber walls 554. The surface coating 504 is provided to coat the chamber wall 554 and other components to provide robustness and lubrication thereto. Additionally, the surface coating prevents ingress of bodily fluids into the device 500. An alternative ultrasonic transducer embodiment disclosed in the Ser. No. 08/739,039 reference comprises a phased array assembly of ultrasonic transducers. In such an embodiment the regenerated cellulose coating is formed over the transducer array as a protective layer. In such ultrasonic applications, it is preferable that the surface coating 504 be substantially ultrasonically transparent, and the regenerated cellulose coating of the present invention satisfies this requirement.

Test of Invention

Samples were built for biocompatibility screening tests. The electrode assembly was a 5.5 F, 10 cm long tubing, pad printed with silver epoxy electrodes and coated with regenerated cellulose. The pad printed silver epoxy electrodes were about 4 mm in length with a 4 mm gap in between each electrode. There were total of 12 electrodes on the assembly. The regenerated cellulose coating was approximately 0.002 inches thick in its dry state. The electrode assembly was attached at both ends of the main body tubing which was a 7 F braided PEBAX tubing. The samples were subject to both MEM elution and hemolysis test at 37° C. and 70° C. to simulate human body temperature and catheter ablation temperature. The samples passed both biocompatibility screening tests. This biocompatibility screening proved that the regenerated cellulose coating was able to contain the silver ions that are otherwise toxic.

To test the electrical characteristics of the coating of the present invention, a diagnostic catheter was coated with regenerated cellulose (Viscose 58, supplied by Applied Technologies Group) to a thickness of approximately 0.002 inches. The impedance between two electrodes was measured using a Hewlett-Packard (HP) impedance analyzer. During the measurement, the distal portion of the catheter was kept in a 0.9% saline solution. At 500 Hz, the impedance between the two electrodes was twice as much as the impedance between another pair of uncoated electrodes. At 500 KHz, the impedance between the two coated electrodes was 50% more than the impedance between the uncoated electrodes.

In another test of an ablation tip, an in-vitro study was conducted of a catheter that had two 12 mm long, pad-printed silver epoxy, electrode rings that were coated with regenerated cellulose having a thickness of approximately 0.002 inches. The ablation test was done in power controlled mode; that is, using an RF generator (EP Technologies Model 1000), the power setting was at 20 watts, and the time setting was at 20 seconds). Two lesions were created by delivering RF energy to two electrodes simultaneously. Both lesions were 5.3 mm in depth and 35.1 mm contiguous in length. Both of these lesions had similar overall dimensions as those created with uncoated electrodes. However, the lesions created with the coated electrodes were more even in depth than were the lesions created with uncoated electrodes.

Coating catheters with the regenerated cellulose significantly reduces manufacturing costs. The use of the coating obviates the need for applying adhesive at the edge of electrode rings or coils used for pacing, recording and ablation. The coating also holds the electrodes in place. The cellulose material itself is very inexpensive, even when adding in costs of processing materials and disposing chemical wastes. Also, the process of dipping and curing the regenerated cellulose coating is more easily automated than the process of placing adhesive at each electrode edge.

The process of coating catheter tip electrodes with regenerated cellulose permits the use of much less expensive electrode technologies than are currently used. Therefore, instead of using platinum electrode rings or stainless coil electrodes, electrodes can be made from processes that have previously been rejected because they are not robust enough when directly exposed on a catheter surface. To further reduce manufacturing costs, less labor-intensive methods can be used to bond wires to the electrode surface, where regenerated cellulose is used to create the final catheter external surface.

Coating catheters with regenerated cellulose can also bring significant clinical benefits. The coated catheter distal portion has fewer edges and corners for protein and other biological material to adhere or stick to. Functionally, the coating provides a smoother physical transition at electrode edges to prevent electrodes from catching on sheaths or from causing abrasive injury to endothelial surfaces. Additionally, the coating, once hydrated, increases the lubricity of the catheter surface. The regenerated cellulose coating prevents blood and protein from leaking into the catheter through various openings that are now coated over. Materials such as silver or copper, which are normally somewhat toxic, have much reduced toxicity after the catheters are coated, since the diffusional distance to tissues is increased substantially and a lower percentage of the metallic surface is even indirectly exposed to the tissue.

What is claimed is:

1. A method for manufacturing a catheter device, comprising:

manufacturing a catheter assembly, including a handle, a guide tube having a proximal end engaged with the handle, and a distal end assembly engaged with a distal end of the guide tube;

applying an active electrode element on the distal end assembly by a process selected from the group consisting of electroplating, vapor deposition, IBAD and pad printing; and applying a regenerated cellulose coating over the distal end assembly.

2. The method of claim 1, wherein the regenerated cellulose coating is applied by applying a viscous coating solution to the distal end assembly; and drying the coating.

3. The method of claim 1, wherein the regenerated cellulose coating is applied by applying a viscous liquid coating to the catheter distal end assembly;

regenerating the viscous coating; and curing the regenerated coating.

4. The method of claim 3, further comprising hydrating the cured coating.

5. A method for manufacturing a catheter device, comprising:

applying an electrode element to an external surface of a catheter body member by a process selected from the group consisting of electroplating, vapor deposition, IBAD and pad printing; and applying a regenerated cellulose surface coating to the electrode element.

* * * * *

UNITED STATES PATENT AND TRADEMARK OFFICE
CERTIFICATE OF CORRECTION

PATENT NO. : 6,357,447 B1
DATED : March 19, 2000
INVENTOR(S) : David K. Swanson, Yi Yang, James G. Whayne and Josef V. Koblish It is certified that error appears in the above-identified patent and that said Letters Patent is hereby corrected as shown below:

<u>Title page,</u>
Item [63], Related U.S. Application Data, change "08/836,174" to -- 08/636,174 --
Item [60], change "60/010,356" to -- 60/010,354 --

Signed and Sealed this

Twenty-fourth Day of September, 2002

*Attest:*

*Attesting Officer*

JAMES E. ROGAN
*Director of the United States Patent and Trademark Office*